United States Patent [19]

Sarrazin et al.

[11] Patent Number: 5,364,998
[45] Date of Patent: Nov. 15, 1994

[54] PROCESS FOR THE SELECTIVE HYDROGENATION OF HYDROCARBONS

[75] Inventors: Patrick Sarrazin, Rueil Malmaison; Jean-Paul Boitiaux, Poissy, both of France

[73] Assignee: Institut Francais Du Petrole, Rueil Malmaison, France

[21] Appl. No.: 42,178

[22] Filed: Apr. 2, 1993

[30] Foreign Application Priority Data

Apr. 2, 1992 [FR] France ................... 92 04150

[51] Int. Cl.⁵ ............................................. C07C 5/05
[52] U.S. Cl. ..................... 585/259; 585/258; 585/273
[58] Field of Search ............... 585/258, 259, 273, 274

[56] References Cited

U.S. PATENT DOCUMENTS

| | | | |
|---|---|---|---|
| 4,337,329 | 6/1982 | Kubo et al. | 525/339 |
| 4,602,000 | 7/1986 | Dupin et al. | 502/335 |

FOREIGN PATENT DOCUMENTS

| | | |
|---|---|---|
| 2091114 | 1/1972 | France . |
| 2103122 | 4/1972 | France . |
| 2594711 | 8/1987 | France . |
| 1004316 | 9/1954 | Germany . |
| 1115238 | 2/1957 | Germany . |
| 0871804 | 6/1961 | United Kingdom . |

OTHER PUBLICATIONS

Derwent Abstract of JP-A-56 081 306.
Derwent Abstract of FR-A-2 103 122.
Derwent Abstract of JP-A-11 10 594.
Derwent Abstract of FR-A-2 594 711.

*Primary Examiner*—Asok Pal
*Assistant Examiner*—P. Achutamurthy
*Attorney, Agent, or Firm*—Millen, White, Zelano & Branigan

[57] ABSTRACT

A process for the selective hydrogenation of unsaturated hydrocarbons is characterized in that the catalyst contains a group VIII metal and an element chosen from within the group constituted by gallium and indium.

21 Claims, No Drawings

PROCESS FOR THE SELECTIVE HYDROGENATION OF HYDROCARBONS

BACKGROUND OF THE INVENTION

Numerous processes for the production of olefins, such as steam cracking, catalytic cracking and viscoreduction produce fractions polluted by molecules more unsaturated than the sought olefins. The satisfactory use of these fractions for producing finished products involves the elimination of these molecules which contain conjugate double bonds and/or triple bonds. The selective hydrogenation of the latter into the corresponding olefins is the preferred process for removing these, while still recovering the sought olefins.

These hydrogenation reactions are generally performed in a temperature range between 20° and 200° C. under a pressure between 10 and 100 bar (1 and 10 megapascal) and with a space velocity between 1 and 40 $m^3/m^3$ of catalyst/h. The catalysts generally used are constituted by one or more metals deposited on an oxide support. The preferred base metals are those of group VIII and more particularly nickel, palladium and platinum. The supports are often chosen among alumina, silica, silica-aluminas, aluminates or charcoal.

The industrial use of such catalysts often takes place in the presence of additives for the purpose of improving the selectivity of the hydrogenation reaction. The most widely used compound is carbon monoxide, as claimed in EP-81,041.

The development of catalysts with better performance characteristics from the activity and selectivity standpoints has led to the introduction of other metals into the catalytic formulations. Reference can e.g. be made to silver (U.S. Pat. No. 4,409,410) and gold (U.S. Pat. No. 4,490,481), which very significantly improve the catalytic properties of group VIII metals for the hydrogenation reaction.

SUMMARY OF THE INVENTION

It has now been discovered in the present invention that it is possible to carry out the hydrogenation of unsaturated diolefin and acetylene compounds with high selectivities into the corresponding olefin compounds without reducing tie activity of the base metal (i.e. of group VIII), with promotion and without using additives in the reaction medium or the preparation of a bimetallic alloy. Working takes place in a continuous or discontinuous reactor in the presence of hydrogen under a total pressure between 10 and 100 bars (1 and 10 megapascal) and preferably between 20 and 80 bars (2 and 8 megapascal), although it is possible without disadvantage to work e.g. up to 300 bars (30 megapascal) at a temperature between 0° and 200° C. and preferably between 30° and 120° C. in the presence of a novel metal catalyst. The latter catalyst contains (a) at least one group VIII metal chosen from among nickel, palladium, platinum, rhodium and ruthenium (palladium, platinum and nickel being the preferred metals) and whose weight percentage is chosen between 0.1 and 10% and preferably between 0.2 and 5% and (b) at least one additional metal element chosen from within group IIIA constituted by gallium and indium, whose weight percentage is chosen between 0.01 and 10% and preferably between 0.1 and 5% and the molar ratio of the metal element of group III no the metal of group VIII is advantageously between 0.2 and 5 and preferably between 0.3 and 2 and (c) a support chosen from within the group constituted by a silica, an alumina, a silica-alumina, an aluminate and a charcoal. Advantageously, the aluminates of the elements of groups I.A, II.A or II.B of the periodic classification can be used, such as e.g. aluminates of Ca, Mg, Ba, Zn, Na, K and Cd and mixed aluminates.

The catalyst can be prepared by different procedures. A preferred procedure is the impregnation of the support, but the invention is not limited to a given procedure. For example, impregnation consists of contacting the preshaped support and an aqueous or organic solution of a compound of the chosen group IIIA metal or metals (gallium and indium), the solution volume being in excess compared with the retention volume of the support or is preferably equal to said volume. After maintaining contact between the support and the solution for several hours, the impregnated support is filtered, washed with distilled water, dried and calcined under air normally at between 110° and 600° C. and preferably between 110° and 500° C. Before depositing the group VIII metal or metals, it is possible to advantageously reduce the catalyst under hydrogen. Working normally takes place at between 50° and 600° C. and preferably between 90° and 500° C., or with the aid of a dissolved organic reducing agent. This operation makes it possible to further increase the activity of the catalyst.

The product obtained is then impregnated by an organic solution (e.g. hydrocarbon solution) or an aqueous solution of a group VIII metal, as a function of the nature of the precursor used. In a particularly advantageous manner, use is made of a solution of nickel or palladium nitrate in water.

The thus impregnated support is filtered, optionally washed with distilled water, dried and calcined under air normally at between approximately 110° C. and approximately 600° C. and preferably between approximately 110° C. and approximately 500° C. It is then reduced under hydrogen at a temperature normally between approximately 50° C. and approximately 600° C. and preferably between approximately 80° C. and approximately 500° C. The group VIII and III elements are then in oxide and/or metal form deposited on the support.

Another method consists of mixing the moist powder of the support with the precursors of the catalyst, followed by shaping and drying.

Examples of metal precursors used in the preparation of the catalyst are given below. For the group VIII metal it is possible to use compounds such as chlorides, nitrates, haloamine compounds, amino compounds, as well as the salts of organic acids soluble in the impregnation solvent. It is also possible to use metalorganic compounds of a group VIII metal in solution in an organic solvent, e.g. a hydrocarbon. As examples of hydrocarbons reference can be made to saturated paraffin hydrocarbons, whose hydrocarbon chain contains 6 to 12 carbon atoms per molecule, naphthene hydrocarbons containing 6 to 12 carbon atoms per molecule or aromatic hydrocarbons containing 6 to 12 carbon atoms per molecule. As examples of metalorganic compounds of the group VIII metals reference can be made to carbonyl, halocarbonyl and acetyl acetonate compounds, without this list being limitative.

The element chosen from within the group constituted by gallium and indium is preferably introduced in the form of at least one inorganic compound chosen from within the group formed by chlorides, nitrates, haloamine compounds, amino compounds and salts of organic acids soluble in impregnation solvents.

The IIIA group metal is advantageously introduced with the aid of an aqueous solution of the inorganic compound of said IIIA group metal. The element chosen from within the group constituted by gallium and indium can also be introduced by means of metalorganic compounds dissolved in an organic solvent, e.g. a hydrocarbon. As examples of hydrocarbons reference can be made to saturated paraffin hydrocarbons, whose hydrocarbon chain contains 6 to 12 carbon atoms per molecule. naphthene hydrocarbons containing 6 to 12 carbon atoms per molecule or aromatic hydrocarbons containing 6 to 12 carbon atoms per molecule. As examples of metalorganic compounds of the metal of the group constituted by gallium and indium reference can be made to alkyls, alkoxides, acetates and acetyl acetonates without this list being in any way limitative.

As stated hereinbefore, the support can be of different types. A particularly suitable support has specific characteristics such as a specific area determined by the B.E.T. method between 10 and 500 m²/g and preferably between 50 and 500 m²/g and a total pore volume of 0.2 to 1.3 cm³/gramme of support.

Once the metals have been fixed to the support, the catalyst advantageously undergoes an activation treatment under hydrogen and at high temperature, e.g. 50° to 600° C., in order to obtain an active metal phase. The procedure of this treatment under hydrogen e.g. consists of slowly raising the temperature under a hydrogen stream up to the maximum reduction temperature e.g. between 50° and 600° C. and preferably between 80° and 500° C., followed by the maintaining thereof for e.g. 1 to 6 hours.

The following non-limitative examples illustrate the invention.

EXAMPLE 1 (Comparative)

The aim of this example is to hydrogenate a charge constituted by 10% by weight butadiene in heptane. The reaction is performed in a perfectly stirred, Grignard-type discontinuous reactor under a pressure of 20 bar and a temperature of 20° C. The hydrogen used is free from carbon monoxide.

The catalyst used, called catalyst A, is constituted by palladium with a content of 0.3% by weight deposited on transition alumina with a specific surface of 70 m²/g. It is prepared by the dry impregnation of a tetragonal gamma alumina of pore volume 0.6 cm³/g with the aid of a palladium nitrate solution. After impregnation, the sample is dried at a temperature of 120° C. for 2 hours and is then calcined under an air flow at 450° C. for 2 hours. Before testing the catalyst is reduced under a hydrogen flow at a temperature of 150° C. for 2 hours.

As the reaction progresses samples are regularly taken and analysed by gas chromatography so as to follow the transformation of the butadiene into butenes and butane. The results obtained are given in the following table:

| Time (min.) | Butadiene (wt. %) | Butenes (wt. %) | Butane (wt. %) |
| --- | --- | --- | --- |
| 0 | 100 | — | — |
| 1 | 80.85 | 19.1 | 0.05 |
| 2 | 75.75 | 24.15 | 0.1 |
| 3 | 66 | 33.85 | 0.15 |
| 4 | 54.5 | 45.33 | 0.17 |
| 5 | 43 | 56.8 | 0.2 |

-continued

| Time (min.) | Butadiene (wt. %) | Butenes (wt. %) | Butane (wt. %) |
| --- | --- | --- | --- |
| 6 | 32 | 67.7 | 0.21 |
| 7 | 20.5 | 79.28 | 0.22 |
| 8 | 9 | 90.7 | 0.3 |

EXAMPLE 2 (according to the invention

In this example the same reaction is performed under the same conditions as in Example 1, but on this occasion use is successively made of different catalysts containing 0.3% by weight palladium and a variable gallium content. The support used is identical to that of the monometallic catalyst A of Example 1. Different batches of this support are dry impregnated by gallium nitrate solutions having variable concentrations.

After impregnation, the samples are dried at a temperature of 120° C. for 2 hours and then calcined under an air flow at a temperature of 450° C. and for 2 hours. This is followed by the deposition of the palladium using the same method as described in Example 1 for catalyst A. Before testing the catalysts are reduced under a hydrogen flow at a temperature of 150° C. and for 2 hours.

The following table gives the composition of the product after 8 minutes of reaction for each of the catalysts indicated by their gallium content, as well as the monometallic catalyst A of Example 1.

| Ga Content (wt. %) | Butadiene (wt. %) | Butenes (wt. %) | Butane (wt. %) |
| --- | --- | --- | --- |
| 0 | 9 | 90.7 | 0.3 |
| 0.07 | 6.57 | 93.16 | 0.27 |
| 0.21 | 5.55 | 94.2 | 0.25 |
| 0.42 | 7.5 | 92.22 | 0.28 |
| 0.82 | 8 | 91.7 | 0.3 |
| 1.19 | 10.3 | 89.4 | 0.3 |

It Can be seen that the catalysts with a gallium content between 0.07 and 0.82% by weight have a superior activity to that of the monometallic catalyst, because at the end of the same reaction time (8 minutes), the butadiene content of the product is lower. Moreover, in can be seen that these catalysts which are more active than the monometallic catalyst are also more selective with respect to the hydrogenation of the butenes. Thus, although the butadiene conversion is greater, it can be seen that the butene content is higher and the butane formation is reduced.

EXAMPLE 3 (according to the invention)

This example uses the same reaction and the same conditions as in Example 1. On this occasion use is made of a catalyst B containing 0.3% by weight palladium and 0.24% by weight gallium deposited on the same support as in Example 1 and following the same preparation method as in Example 2. Use is also made of a catalyst C having the same composition, but which differs from catalyst B by the fact that the gallium precursor on alumina used during the preparation has been reduced under hydrogen at a temperature of 450° C. and for 2 hours prior to palladium deposition. The composition of the products obtained after 8 minutes of reaction is given in the following table:

| Catalyst | Butadiene (wt. %) | Butenes (wt. %) | Butane (wt. %) |
|---|---|---|---|
| B | 5.6 | 94.14 | 0.26 |
| C | 4.2 | 95.53 | 0.27 |

It Can be seen that the catalyst C is more active than catalyst B with respect to the hydrogenation of butadiene. There is also a selectivity improvement, because with a higher butadiene conversion, the butene content is higher for catalyst C.

EXAMPLE 4 (comparative)

The aim of this example is to hydrogenate a $C_3$ steam cracking fraction having the following composition:
Propane=3.59%
Propylene=92.14%
Allylene (MA)=1.78%
Propadiene (PD)=1.65%.

The reaction is performed in the liquid phase in a continuous fixed bed reactor under a pressure of 24 bar and a temperature of 50° C. The space velocity is 20 $cm^3$ of charge/$cm^3$ of catalyst/h and the molar ratio of hydrogen to allylene, plus propadiene=1.2. The hydrogen used is free from carbon monoxide.

The catalyst used is catalyst A of Example 1.

Product samples are regularly taken and analysed by gas chromatography so as to follow the conversion of allylene and propadiene, as well as the propylene content. The results obtained are given in the following table:

| Time (hours) | Propylene (wt. %) | Allylene (wt. %) | Propadiene (wt. %) |
|---|---|---|---|
| 50 | 94.87 | — | 0.071 |
| 100 | 94.92 | — | 0.069 |
| 150 | 95.13 | — | 0.080 |
| 200 | 94.78 | — | 0.052 |
| 300 | 94.90 | — | 0.065 |

On calculating the average propadiene and propylene contents during the operation, it is possible to calculate the average allylene and propadiene conversion, as well as the average propylene gain. In this example there is a 98% conversion and a propylene yield, expressed by the ratio of the propylene content of the product to the propylene content of the charge, of 103%.

EXAMPLE 5 (according to the invention)

This example uses the same reaction under the same conditions as in Example 4, but in the presence of catalyst C of Example 3. The analysis results obtained are given in the following table:

| Time (hours) | Propylene (wt. %) | Allylene (wt. %) | Propadiene (wt. %) |
|---|---|---|---|
| 50 | 95.41 | — | 0.0072 |
| 100 | 95.43 | — | 0.0089 |
| 150 | 95.39 | — | 0.0070 |
| 200 | 95.05 | — | 0.0090 |
| 300 | 95.56 | — | 0.0060 |

In this example there is a 99.78% conversion and a propylene yield, expressed by the ratio of the propylene content of the product to the propylene content of the charge, of 103.5%.

EXAMPLE 6 (comparative)

This example uses the same reaction under the same conditions as in Example 1, but in this case successive use is made of different catalysts containing 0.3% by weight palladium and a variable gallium content. The support used is identical to that of the monometallic catalyst A of Example 1. Different batches of this support are impregnated dry by, palladium nitrate using the same method as described for catalyst A in Example 1. This is followed by the deposition of the gallium by impregnation of gallium nitrate solutions having variable concentrations. After impregnation, the samples are dried at a temperature of 120° C. for 2 hours, then calcined under an air flow at a temperature of 450° C. for 2 hours. Prior to testing, the catalysts are reduced under a hydrogen flow at a temperature of 150° C. for 2 hours.

The following %able gives the composition of the product after 8 minutes reaction for each of the catalysts indicated by their gallium content, as well as for the monometallic catalyst A of Example 1.

| Ga content (wt. %) | Butadiene (wt. %) | Butenes (wt. %) | Butane (wt. %) |
|---|---|---|---|
| 0 | 9 | 90.7 | 0.3 |
| 0.08 | 7.57 | 92.14 | 0.29 |
| 0.23 | 5.95 | 93.78 | 0.27 |
| 0.41 | 8.5 | 91.22 | 0.28 |
| 0.80 | 8.6 | 91.1 | 0.3 |
| 1.22 | 10.2 | 89.49 | 0.31 |

It can be seen that the samples with a gallium content between 0.08 and 0.80% by weight .have a superior activity to that of the monometallic catalyst of Example 1, because following the same reaction time (8 minutes), the butadiene content of the product is lower. Moreover, it can be seen that the catalysts more active than the monometallic catalyst are also more selective with respect to the butene hydrogenation. Thus, although the butadiene conversion is higher, the butene content is greater and the butane formation is reduced.

We claim:

1. A process for the selective hydrogenation of diolefins in a charge consisting essentially of monoolefins and, as impurities, diolefins, comprising contacting the charge and hydrogen with a supported catalyst at a temperature between 0° and 200° C. and a pressure between 20 and 300 bars in the absence of carbon monoxide, said catalyst, based on its total weight, containing:
   a) 0.1 to 10% of at least one group VIII metal chosen from within the group consisting of nickel, palladium, platinum, rhodium and ruthenium;
   b) 0.01 to 10% of at least one additional metal of group IIIA chosen from within the group consisting of gallium and indium.

2. Process according to claim 1, wherein the group VIII metal is palladium, platinum or nickel.

3. A process according to claim 2, wherein the support is a silica, an alumina, a silica-alumina, an aluminate of an alkali metal, or of an alkaline earth metal, or of zinc, or of cadmium, or a mixture of said aluminates.

4. A process according to claim 1 wherein the group VIII metal concentration is between 0.2 and 5% by weight.

5. A process according to claim 1 wherein the group IIIA metal concentration is between 0.1 and 5% by weight.

6. A process according to claim 1 wherein the molar ratio of the group IIIA metal to group VIII metal is between 0.2 and 5.

7. A process according to claim 6, wherein the molar ratio is between 0.3 and 2.

8. A process according to claim 1, wherein the supported catalyst is formed by the deposition of the group IIIA metal on the support, followed by the deposition of the group VIII metal.

9. A process according to claim 8, wherein the support impregnated by the group IIIA metal undergoes a reduction prior to the deposition of the group VIII metal.

10. A process according to claim 1, wherein the group IIIA metal is gallium.

11. A process according to claim 1, wherein the group IIIA metal is indium.

12. A process according to claim 2, wherein the group IIIA metal is gallium.

13. A process according to claim 2, wherein the group IIIA metal is indium.

14. A process according to claim 12, wherein the support is a silica, an alumina, a silica-alumina, an aluminate of an alkali metal, alkaline earth metal, zinc or cadmium, or a mixture of said aluminate.

15. A process according to claim 13, wherein the support is a silica, an alumina, a silica-alumina, an aluminate of an alkali metal, alkaline earth metal, zinc or cadmium, or a mixture of said aluminates.

16. A process according to claim 14, wherein the group VIII metal concentration is between 0.2% and 5% by weight.

17. A process according to claim 15, wherein the group VIII metal concentration is between 0.2% and 5% by weight.

18. A process according to claim 16, wherein the group IIIA metal concentration is between 0.1% and 5% by weight.

19. A process according to claim 17, wherein the group IIIA metal concentration is between 0.1% and 5% by weight.

20. A process according to claim 1, wherein the charge consists essentially of butenes contaminated by butadiene.

21. A process according to claim 1, wherein the charge consists essentially of propylene contaminated by propadiene.

* * * * *